United States Patent [19]

Timm

[11] Patent Number: 5,279,168

[45] Date of Patent: Jan. 18, 1994

[54] PROBE APPARATUS

[76] Inventor: Stephen D. Timm, 3040-125th Ave., SE., #10, Bellevue, Wash. 98005

[21] Appl. No.: 816,373

[22] Filed: Dec. 30, 1991

[51] Int. Cl.$^5$ ............... G01N 27/90; G21C 17/017; G01M 19/00
[52] U.S. Cl. .................. 73/866.5; 165/11.2; 324/220
[58] Field of Search ............ 73/866.5, 865.8, 865.9; 324/220, 221, 222; 376/249; 165/11.1, 11.2, 76

[56] References Cited

U.S. PATENT DOCUMENTS

| | | | |
|---|---|---|---|
| 3,916,302 | 10/1975 | Madewell | 324/220 |
| 3,994,173 | 11/1976 | Ward et al. | 73/866.5 |
| 4,153,875 | 5/1979 | Pigeon et al. | 324/220 |
| 4,303,884 | 12/1981 | Malick | 324/220 |
| 4,448,912 | 5/1987 | Junker | 324/220 |
| 4,851,773 | 7/1989 | Rothstein | 324/220 |
| 4,856,337 | 8/1989 | Metala et al. | 73/601 |
| 5,025,215 | 6/1991 | Pirl | 73/866.5 X |
| 5,174,164 | 12/1992 | Wilheim | 376/249 X |
| 5,174,165 | 12/1992 | Pirl | 73/866.5 |

FOREIGN PATENT DOCUMENTS

| | | | |
|---|---|---|---|
| 90725 | 10/1983 | European Pat. Off. | 165/11.2 |
| 191058 | 8/1988 | Japan | 73/866.5 |
| 7510608 | 3/1976 | Netherlands | 73/866.5 |
| 1488833 | 10/1977 | United Kingdom | 324/220 |

OTHER PUBLICATIONS

Zetec Probe Catalog, Zetec, Inc., Jan. 1, 1991 "Bobbin Probes" 1 page.
Zetec Eddy Current Product Guide, Zetec, Inc., 1987 "Testers, Systems and Probes from the eddy current authority", 4 pages.

Primary Examiner—Tom Noland

[57] ABSTRACT

A probe assembly for inspection and/or repair of heat exchanger tubing is provided by a sensor deployed by an elongate flexible sensor support cable and a plurality of bushings forming a flexible coaxial sheath about the sensor support cable. Bushing retainers are secured to the sensor support member to retain spacing between the bushings during forceful deployment and retraction of the assembly.

21 Claims, 6 Drawing Sheets

PROBE APPARATUS

BACKGROUND OF THE INVENTION

This invention relates to inspection and/or repair apparatus, and more particularly, a flexible shaft and probe used to inspect and/or repair the interior o longitudinally curved tubular members and passageways.

Hazardous environments often limit human access to particular locations. The inspection and repair of nuclear steam generators often requires remote accessing of critical components. Nuclear steam generators, for example, include a vertically oriented shell, a heat exchanger in the form of a bundle of u-shaped tubes disposed in the shell, a tube sheet that supports the tubes at the ends opposite the u-shaped curvature, and a dividing plate that cooperates with the tube sheet and forms a primary fluid inlet plenum at one end of the tube bundle and a primary fluid outlet plenum at the other end of the tube bundle.

Radioactive primary fluid, once heated by circulation through the core of the nuclear reactor, enters the steam generator through the primary fluid inlet plenum. From there the primary fluid flows upwardly through first openings located in the u-shaped tubes near the tube sheet, then through the u-shaped tube curvatures, downwardly through second openings in the u-shaped tubes near the tube sheet, and into the primary fluid outlet plenum. At the same time, secondary fluid, known as feed water, is circulated around the exterior of the u-shaped tubes to cause heat transfer from the primary fluid to the feed water. A portion of the secondary fluid (feed water) is converted into steam. The walls of the u-shaped tubes and tube sheet isolate the secondary fluid from the radioactive primary fluid. It is thus important that the u-shaped tubes and tube sheet be maintained defect free so that no breaks occur in the u-shaped tubes or in the welds between the u-shaped tubes and the tube sheet that could lead to leakage and hence cause contamination of the secondary fluid by the radioactive primary fluid.

In order to either inspect or repair the u-shaped tubes or the tube sheet welds by way of access through the primary fluid inlet and outlet plena, manways are provided in the vertical shell so that working personnel may enter the inlet and outlet plena. However, the radioactive primary fluid often contaminates the inlet and outlet plena, thereby limiting the time in which working personnel may occupy this area. It is thus advantageous to perform inspection or repair of the u-shaped tubes and tube sheet without requiring the presence of working personnel. The following are exemplary of mechanisms known in the art that attempt to provide a solution to this problem, but all have shortcomings.

U.S. Pat. No. 4,303,884, issued to Malick, discloses an inspection probe or sensor for inspecting tubular members comprised of a plurality of axially oriented plastic strips which form the circumference of the probe, with each plastic strip having mounted thereon an eddy current coil. A rubber tube is disposed on the interior of the plastic strip so that when the rubber tube is inflated, the plastic strips and coils are forced outward into close contact with the tubular member so that the eddy current coils can detect flaws in the tubular member.

U.S. Pat. No. 4,668,912, issued to Junker, teaches an inflatable eddy current inspection probe having a molded central body with a plurality of eddy current coils and leads imbedded therein. The central body is expanded a will by introduction of water or air through a pressure hose connected to the central body to produce effective contact between the coils and the inside wall of the tube.

The above two types of inspection probes or sensors are part of a probe assembly that is pushed longitudinally from one end of the u-shaped tubes to the other by an element of the probe assembly known as the positioning shaft. However, positioning shafts known in the art are inadequate for pushing a probe assembly through u-shaped tubes having curves of relatively small radii. When the probe assembly encounters such sharp curves, frictional resistance to the probe assembly develops large lengthwise compressive forces in the positioning shaft causing it to buckle. This in turn generates side loads against the interior of the tube risking damage to the tube structure and increasing the frictional resistance to lengthwise movement of the assembly. Also, buckling of the positioning shaft makes the inspection and/or repair more difficult, consumes critical time, and often damages the probe assembly itself.

One type of probe assembly positioning shaft known in the art is a flexible polymer tube having a round cross-section and a hollow core. Carried within this core are a plurality of electrical instrumentation conductors and a flexible stainless steel emergency retrieval cable used to retrieve sensors that have become disconnected from the positioning shaft. However, known polymer positioning shafts suffer from an inability to resist buckling when subjected to typical compressive forces. Also, the polymer positioning shaft suffers from undesirable weakening when high temperatures are encountered in the heat exchanger tubes.

A second type of positioning shaft for probe assemblies is a helically wound metal casing having a continuous polymer coating. Some of these types of positioning shafts have a polymer coating that is not thick enough to resist buckling by compressive forces. Other positioning shafts of this type have a polymer coating that is so thick the positioning shaft cannot be bent sufficiently to negotiate bent tubes having curves of low radii.

Another known positioning shaft uses a helically wound metal casing, without a polymer coating. This type scores or scratches the interior of the heat exchanger tubes, and cannot be rolled for storage without risking the abrasion of the electrical instrumentation conductors of the probe assembly sensor.

A need thus exists for a positioning shaft of a probe assembly capable of traversing ben tubes having curvatures with small radii and similar small passageways having either a single sharp bend or a series of lesser bends or curves. A need also exists for a positioning shaft of the above type which will not buckle when subjected to lengthwise compressive forces, such as due to pushing on the shaft during positioning, and which will not scratch the interior of the passageway, and which, after removal, can be rolled for storage without abrading the electrical instrumentation conductors and elements of the sensor.

SUMMARY OF THE INVENTION

An elongate probe assembly for deployment in tubing, conduit, pipe or other relatively small passageways includes a slender, flexible member supporting a sensor or other probe device, a plurality of bushings mounted on the support member, and bushing retainers secured at axial positions along the member for maintaining the spacing of the bushings. Preferably, the support member is a helically coiled cable having an intercoil tension biasing it into coil-to-coil contact. Additionally, contacting axial surfaces of the cable coils are shaped to resist buckling in reaction to lengthwise compressive forces encountered during deployment.

Also in the preferred embodiment of the invention, the bushings mounted on the cable have contacting axial ends so shaped that the bushings further resist buckling of the cable due to the compressive forces.

As further preferred features, the bushing retainers have a maximum radial dimension less than the outside diameter of the bushings, the cable and retainers are made of a relatively strong metal alloy such as a high grade steel, and the bushings are comprised of a synthetic polymer such as of a polyamide.

BRIEF DESCRIPTION OF THE DRAWINGS

These and further objects, features, and advantages of the invention will become apparent from reading the following detailed description in conjunction with the attached drawings in which.

DETAILED DESCRIPTION OF THE PREFERRED EMBODIMENT

Figure 1:
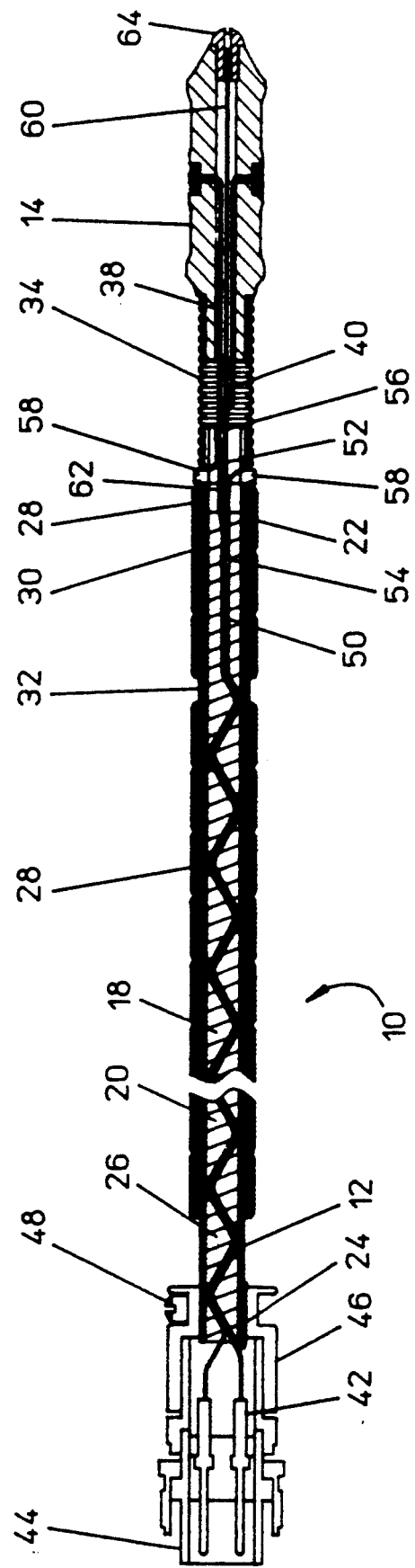
FIG. 1 is an elevational, cross-sectional view of the preferred embodiment of the probe apparatus of the present invention.
Figure 2:
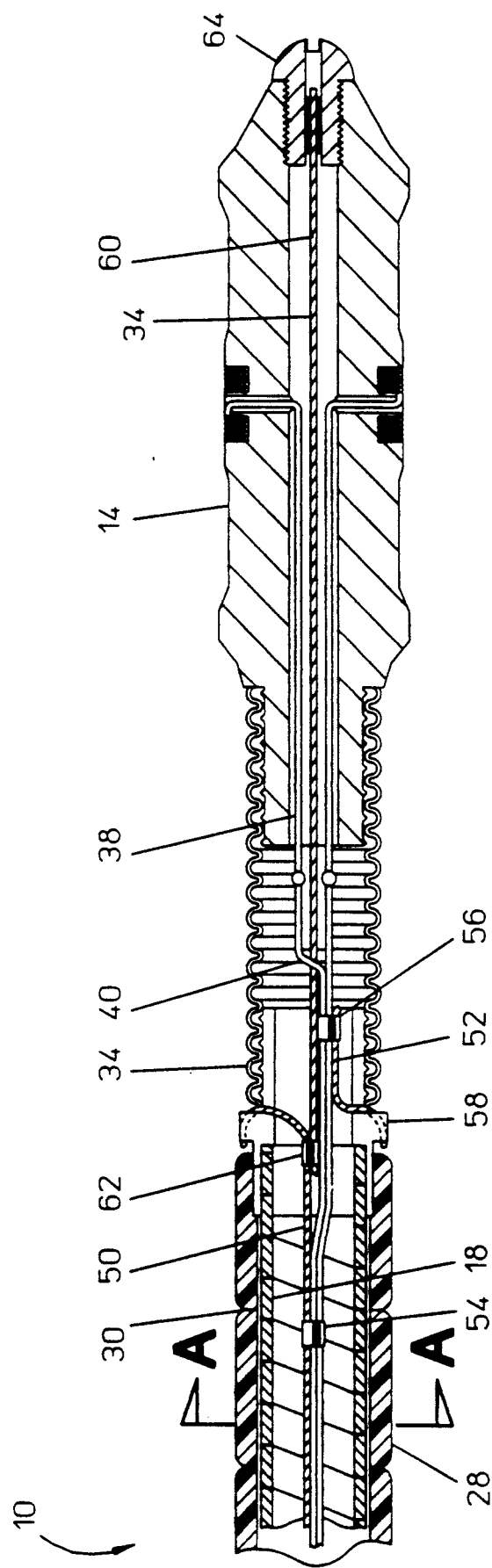
FIG. 2 is an elevational, cross-sectional view in detail of FIG. 1 showing the forward sensor portion of the probe apparatus of the preferred embodiment.
Figure 3:
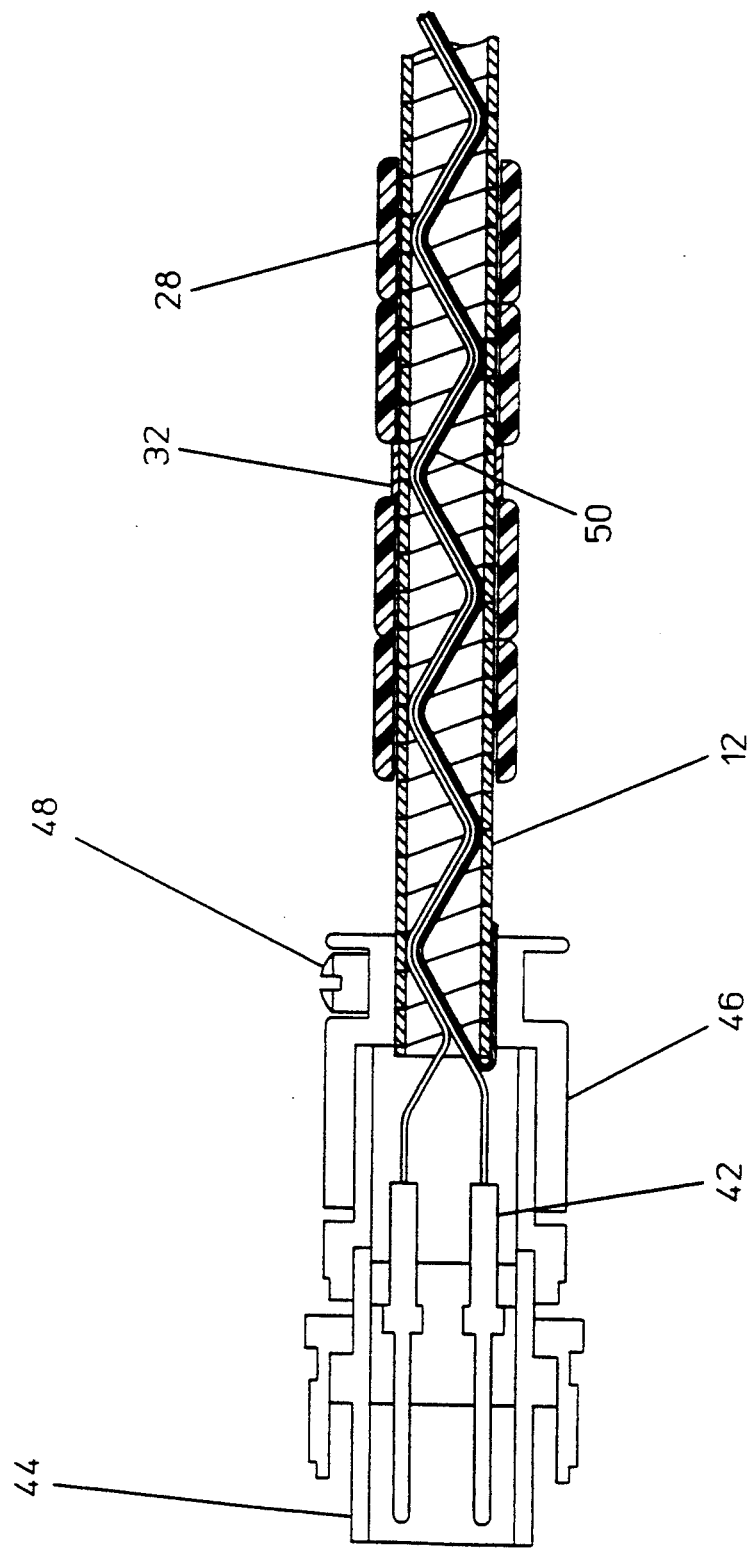
FIG. 3 is an elevational, cross-sectional view in detail of FIG. 1 showing the rear portion of the probe apparatus of the preferred embodiment.

Referring first to FIGS. 1–3, probe assembly 10 of the preferred embodiment includes transversely flexible positioning member or shaft 12 which supports a sensor 14 adjacent a forward end thereof. Shaft 12 is coaxially sheathed by bushings 28 which cooperate with the flexible shaft 12 to facilitate insertion, positioning and retraction of the assembly 10 in small curved passageways such as pipes, tubing and the like. Here, sensor 14 is an eddy current sensor known in the art. However, it is to be understood that the present invention contemplates sensor 14 being of a type other than the eddy current sensor used here, such as a radiographic, ultrasound, capacitive or inductive sensor. Also, in place of sensor 14, other deployable probe devices may be used such as for repair, positioning of instrumentation, measuring, etc.

Positioning shaft 12 is provided by a type of flexible cable 18 known per se, and made of a helically coiled metal alloy such as steel, and has a center bore 26 for instrumentation leads, and a forward end 22 and a rear end 24. In fabricating cable 18, a continuous strip or web of metal, here of rectangular cross-section, is wound helically on a mandrel as known per se. However, other cross-sectional configurations, such as round, square, or oval, for example, may be employed for the starting material. In this case, the helically coiled cable is pretensioned to bias adjacent coils toward coil-to-coil contact (also called close wound) This pre-tensioning of flexible cable 18 allows positioning shaft 12 to resist stretching caused by external tension forces which occur during retraction of positioning shaft 12 from the tube or pipe being inspected. Furthermore, the adjacent coils of flexible helical cable 18 have contacting axial end surfaces 20 that are substantially flat and parallel with one another which allows stable seating of one coil against another. This further allows flexible cable 18 to resist buckling when under compressive force during use.

To further enhance the ability of the assembly 10 to negotiate tight passageways such as sharp bends in heat-exchanger tubing, bushings 28 are mounted coaxially on flexible cable 18. Each of bushings 28 is preferably a separate member discrete from the other bushings 28 and has the shape of an annular bead of axial length about the same as its outside diameter. Bushings 28 are preferably comprised of a material that will not abrade, score, or contaminate the tube, pipe or passageway being inspected. Additionally, it is desirable that bushings 28 be manufactured from a material having superior wear characteristics and a low coefficient of friction. Bushings 28 are here preferably comprised of a synthetic polymer such as, for example, "NYLON" TM of Dupont, a synthetic polyamide. However, it is to be understood that other configurations and materials having the above desired properties can be employed. For example, bushings 28 may alternatively be connected or interposed by flexible hinge strips, webbing or gaskets so that the main bodies of the bushings can articulate, or the bushings may be in a helix with each coil functioning as a bushing unit, flexibly joined by the helix to the adjacent bushing coils. Bushings 28 are annular and preferably have a circular cross-section, but may also have different cross-sections that, for example, match that of the passageways to be inspected. The outside diameter of each bushing 28 is significantly less than that of the inside diameter of the passageway to be inspected so as to freely slip therewithin and negotiate its sharpest bends and curves. The inside diameter and axial length of each of bushings 28 must be such that flexible cable 18 is capable of initial free bending with minimal restriction but still constrain the body of cable 18 against buckling under substantial compression loading.

Adjacent bushing ends on flexible cable 18 have load bearing end surfaces 30 that here are substantially flat and parallel with one another which allows stable seating on contact of one bushing 28 against another such that buckling of positioning shaft 12 is resisted when a compressive force is encountered during tube inspection. Alternatively, end surfaces 30 may be non-flat, grooved or other shapes that mate and transfer compression loads bushing to bushing.

A plurality of bushing retainers 32 are mounted at axial fixed positions on flexible cable 18 for spacing of bushings 28 along flexible cable 18. Bushing retainers 32 are preferably bands of metal alloy crimped or otherwise permanently attached at predetermined locations o the exterior of flexible cable 18 such that each bushing retainer 32 contacts either an adjacent bushing 28 or another bushing retainer 32. The radial extent of bushing retainers 32 is preferably less than the outside diameter of bushings 28 in order to preclude contact and hence abrasion of the tube or pipe being inspected. Bushing retainers 32 insure that the majority of bushings 28 will remain attached to flexible cable 18 of positioning shaft 12 should positioning shaft 12 be severely damaged or even severed during tube inspection. Bushing retainers 32 also minimize the gap that otherwise occurs between adjacent bushings 28 when the positioning shaft 12 is excessively stretched due to large tension forces encountered during retraction of assembly 10 from the pipe or tube being inspected.

In a typical application of assembly 10, flexible guide member 34 connects sensor 14 to a forward end 22 of positioning shaft 12, and allows pivotal movement of sensor 14 with respect to positioning shaft 12. Sensor 14 includes bore 36, through which passes sensor electrical conductors 38 and positioning shaft electrical conductors 40. Sensor electrical conductors 38 and positioning shaft electrical conductors 40 are connected at this forward end 22 of cable 18. Positioning shaft electrical conductors 40 also pass through central bore 26 of flexible cable 18 and connect to electrical terminals 42 in a rear end electrical connector 44. At the cable rear end 24, a split clamp 46 secures connector 44, which is tightened onto flexible cable 18 by screws 48 or the like.

Strain relief cables 50 and 52 are employed to restrict the movement of that portion of positioning shaft electrical conductors 40 flexible guide member 34 where positioning shaft electrical conductors 40 are connected to sensor electrical conductors 38. Strain relief cables 50 and 52 are clamped to positioning shaft electrical conductors 40 by clamps 54 and 56 respectively. Strain relief cable 50 which is longer than strain relief cable 52, extends from end coupler 58 adjacent flexible guide member 34, passes through central bore 26 of flexible cable 18, and attaches at rear end 24 of flexible cable 18 adjacent split clamp 46. Clamp 54 connects strain relief cable 50 to positioning shaft electrical conductors 40 at a location in central bore 26 of flexible cable 18. The length of strain relief cable 50 within central bore 26 of flexible cable 18 is essentially the same as the length of positioning shaft electrical conductors 40 within central bore 26 of flexible cable 18.

Strain relief cable 52 extends from end coupler 58 to a point within flexible guide member 34 where clamp 56 connects strain relief cable 52 to positioning shaft electrical conductors 40. Strain relief cable 60 is connected to strain relief cable 50 by clamp 62, and passes through flexible guide member 34 and bore 36 of sensor 14. Screw 64 in sensor 14 fastens strain relief cable 60 therein such that strain relief cable 60 is able to capture sensor 14 if it becomes dislodged from probe assembly 10.

Figure 4:
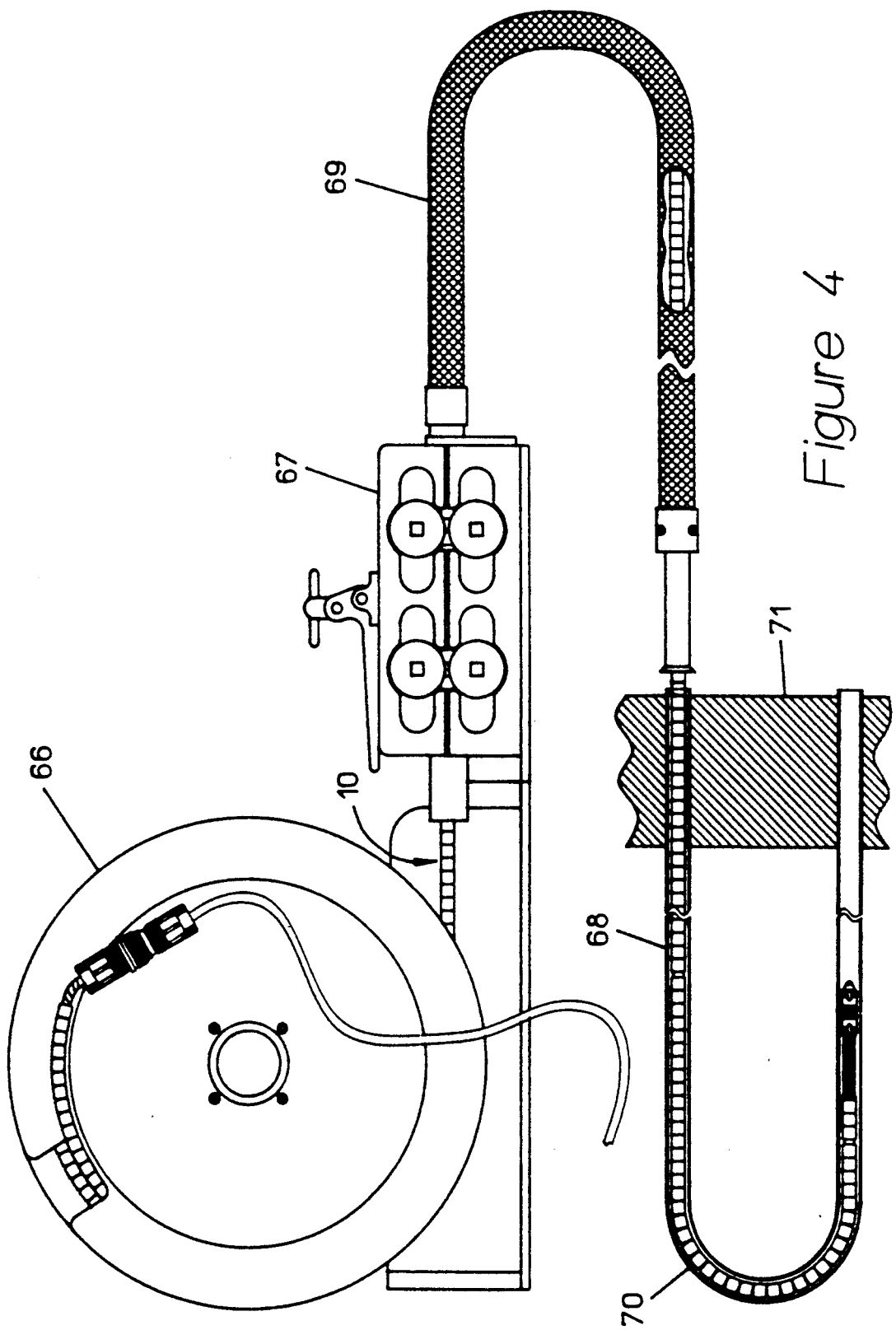
FIG. 4 is a schematic diagram of the probe apparatus of the present invention in a typical application.
Figure 5:
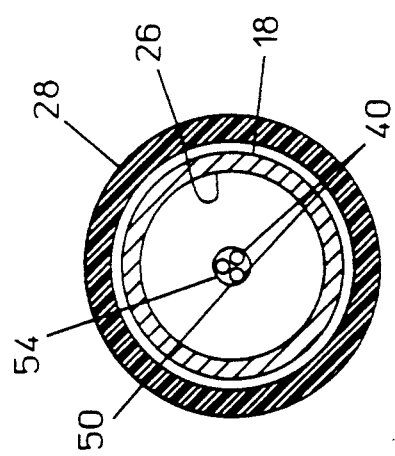
FIG. 5 is a cross section of the probe apparatus of FIG. 1, taken through line 5—5.

Now referring to FIG. 4, the operation of probe assembly 10 is shown. Take-up spool 66, which preferably houses probe assembly 10 in a coiled configuration of approximately 12 inches in diameter, a cable driver/puller 67, and a guide conduit 69 are employed to feed probe assembly 10 into the u-shaped tube 68 supported by a tube sheet 71 of a reactor heat exchanger that is being inspected. Note that u-shaped tube 68 has a relatively narrow radius of curvature 70 which probe assembly 10 is able to negotiate both during forward insertion and, importantly, also in retraction.

Figure 6:
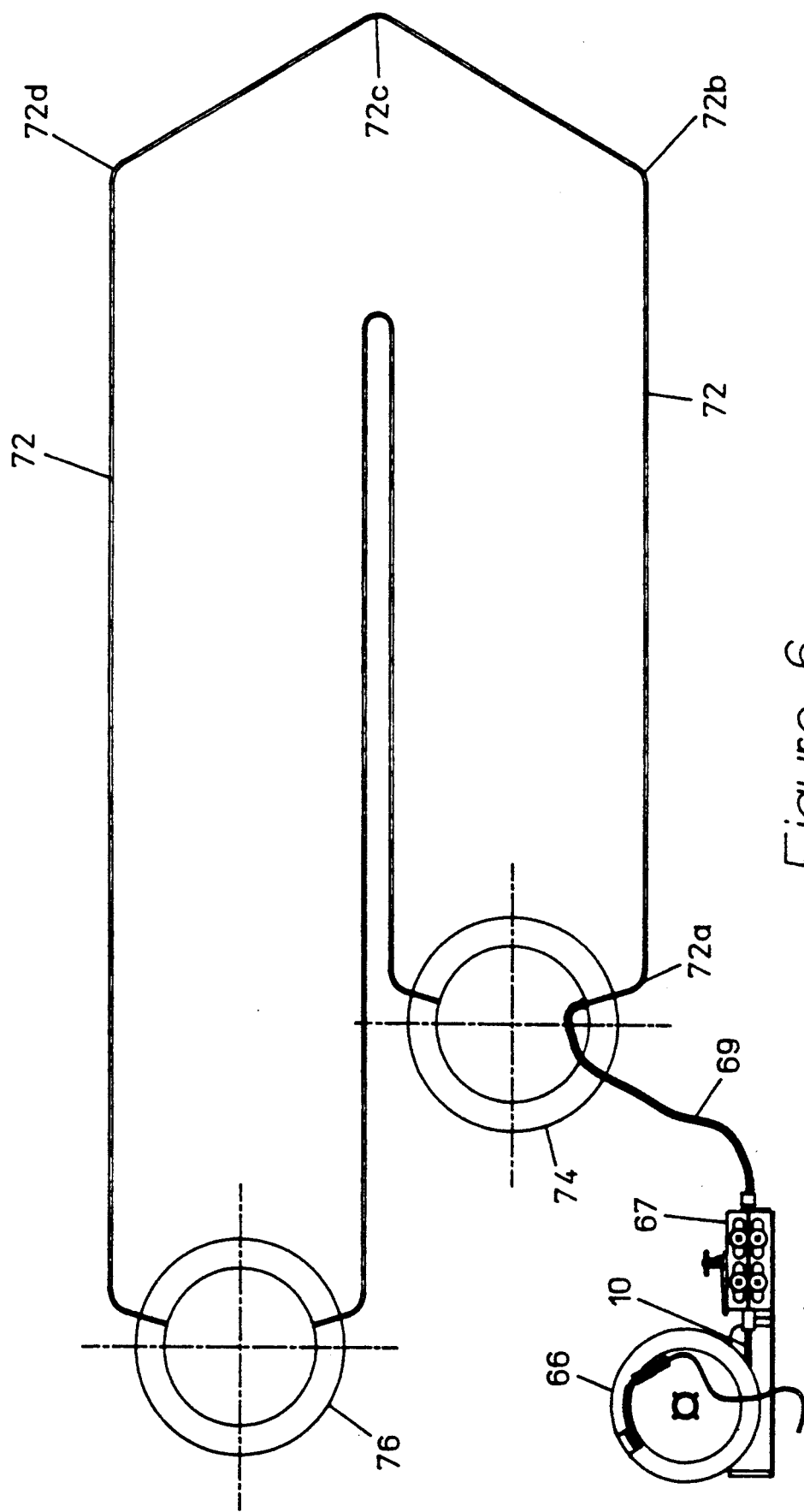
FIG. 6 is another schematic diagram of the probe apparatus used in a different application from that shown in FIG. 4.

FIG. 6 shows another application of prob assembly 10 in which flexible cable 18 supporting sensor 14 must negotiate a succession of multiple bends 72a, 72b, 72c and 72d in fluid piping 72 that interconnects reactor vessels 74 and 76.

While only particular embodiments have been disclosed herein, it will be readily apparent to persons skilled in this art that numerous changes and modifications can be made to this embodiment including the use of equivalent means, devices and method steps, without departing from the spirit of the invention.

I claim:

1. A flexible casing for facilitating movement of a probe device deployed by a flexible slender sensor support member, said flexible casing comprising:
   a plurality of bushings adapted to be axially disposed on the sensor support member; and
   bushing retaining means adapted to be secured to the sensor support member to retain spacing between at least some of said bushings wherein said bushing retaining means has an outer radial extent that is less than the outside diameter of said bushings.

2. The flexible casing of claim 1 wherein said bushings are substantially annular in shape and have substantially flattened parallel axial end surfaces.

3. The flexible casing of claim 1 wherein said bushings are comprised of a synthetic polymer.

4. A passageway inspection and/or repair apparatus comprising:
   a helically coiled cable having a longitudinal axis and adapted to position a sensor in a passageway, said helically coiled cable formed by at least one strand helically wound around said longitudinal axis;
   a plurality of annular cable casing segments axially disposed on said cable, said cable casing segments having an inside diameter greater than the outside diameter of said cable by an amount such that said cable can bend substantially without restriction by said cable casing segments; and
   casing segment retaining means secured on said cable retaining a plurality of said segments against substantial axial movement relative to said cable.

5. The apparatus of claim 4 wherein said helically coiled cable has a tension such that adjacent coils contact and said adjacent coils have substantially parallel contacting edges.

6. The apparatus of claim 4 wherein said cable casing segments that are adjacent have substantially parallel contacting edges.

7. The apparatus of claim 4 wherein said casing segment retaining means has an outside diameter less than the outside diameter of said cable casing segments.

8. The apparatus of claim 4 wherein said cable is comprised of a metal alloy.

9. The apparatus of claim 4 wherein said cable casing segments are comprised of a synthetic polymer.

10. A heat exchanger inspection and/or repair probe assembly for remote deployment in a curved passageway of heat exchanger piping comprising:
    a helically coiled cable having a tension biasing adjacent coils of said cable toward coil-to-coil contact, said adjacent coils having substantially parallel contacting surfaces whereby said contacting surfaces resist buckling of said cable in reaction to a compressive force encountered during inspection;
    a plurality of bushings disposed axially on said cable with adjacent bushings having substantially parallel contacting ends such that said plurality of bushings further resists buckling of said cable in reaction to a compressive force encountered during inspection; and
    bushing retaining means secured at fixed axial positions on said cable for spacing at least some of said bushings along said cable, said bushing retaining means having a maximum radial dimension less than an outside diameter of bushings retained thereby.

11. The probe assembly of claim 10 wherein said cable is comprised of a metal alloy.

12. The probe assembly of claim 10 wherein said bushings are comprised of a synthetic polymer.

13. An eddy current probe assembly comprising:
a helically coiled cable having a longitudinal axis and being formed by at least one strand helically wound around said longitudinal axis;
an eddy current sensor attached to said cable;
a plurality of bushings coaxially disposed on said cable, said bushings having an inside diameter greater than the outside diameter of said cable by an amount such that said cable can bend substantially without restriction by said bushings; and
bushing retaining means secured to said cable and spacing at least some of said bushings.

14. The probe assembly of claim 13 wherein said helically coiled cable has a tension such that adjacent coils contact and said adjacent coils have substantially parallel contacting edges.

15. The probe assembly of claim 13 wherein said bushings that are adjacent have substantially parallel contacting edges.

16. The probe assembly of claim 13 wherein said bushing retaining means has an outside diameter less than the outside diameter of said bushings.

17. The probe assembly of claim 13 wherein said cable is comprised of a metal alloy.

18. The probe assembly of claim 13 wherein said bushings are comprised of a synthetic polymer.

19. A passageway inspection and/or repair apparatus comprising:
a helically coiled cable adapted to position a sensor in a passageway, said helically coiled cable having a tension such that adjacent coils contact and said adjacent coils have substantially parallel contacting edges;
a plurality of annular cable causing segments axially disposed on said cable; and
casing segment retaining means secured on said cable retaining a plurality of said segments against axial movement relative to said cable.

20. A passageway inspection and/or repair apparatus comprising:
a helically coiled cable adapted to position a sensor in a passageway;
a plurality of annular cable casing segments axially disposed on said cable, said cable casing segments that are adjacent having substantially parallel contacting edges; and
casing segment retaining means secured on said cable retaining a plurality of said segments against axial movement relative to said cable.

21. A passageway inspection and/or repair apparatus comprising:
a helically coiled cable adapted to position a sensor in a passageway;
a plurality of annular cable casing segments axially disposed on said cable; and
casing segment retaining means secured on said cable retaining a plurality of said segments against axial movement relative to said cable, said casing segment retaining means having an outside diameter less than the outside diameter of said cable casing segments.

* * * * *